United States Patent [19]

Chu

[11] Patent Number: 4,590,321

[45] Date of Patent: May 20, 1986

[54] AROMATIZATION REACTIONS WITH ZEOLITES CONTAINING PHOSPHORUS OXIDE

[75] Inventor: Chin-Chiun Chu, North Brunswick, N.J.

[73] Assignee: Mobil Oil Corporation, New York, N.Y.

[21] Appl. No.: 744,072

[22] Filed: Jun. 12, 1985

[51] Int. Cl.$^4$ ............................. C07C 1/20; C07C 2/00
[52] U.S. Cl. .................................... 585/415; 585/407; 585/408; 585/469; 585/640
[58] Field of Search ............... 585/415, 407, 408, 469, 585/639, 640

[56] References Cited

U.S. PATENT DOCUMENTS

| | | | |
|---|---|---|---|
| 3,760,024 | 9/1973 | Cattanach | 585/415 |
| 3,899,544 | 8/1975 | Chang et al. | 585/640 |
| 3,911,041 | 10/1975 | Kaeding et al. | 585/640 |
| 3,945,913 | 3/1976 | Brennan et al. | 208/137 |
| 3,972,832 | 8/1976 | Butter et al. | 585/415 |
| 4,016,219 | 4/1977 | Kaeding | 585/415 |
| 4,044,065 | 8/1977 | Butter et al. | 585/415 |
| 4,078,990 | 3/1978 | Brennan et al. | 208/64 |
| 4,137,195 | 1/1979 | Chu | 585/454 |
| 4,152,364 | 5/1979 | Chu | 585/454 |
| 4,157,356 | 6/1979 | Bulford et al. | 585/415 |
| 4,175,057 | 11/1979 | Davies et al. | 502/71 |
| 4,182,923 | 1/1980 | Chu | 585/475 |
| 4,197,214 | 4/1980 | Chen et al. | 585/640 |
| 4,329,533 | 5/1982 | Chu | 585/466 |
| 4,341,622 | 7/1982 | Tabak et al. | 208/66 |
| 4,350,835 | 9/1982 | Chester et al. | 585/415 |
| 4,384,155 | 5/1983 | Chu | 585/466 |
| 4,458,097 | 7/1984 | Garska et al. | 585/415 |
| 4,469,909 | 9/1984 | Chester et al. | 585/481 |

*Primary Examiner*—John Doll
*Assistant Examiner*—A. Pal
*Attorney, Agent, or Firm*—Alexander J. McKillop; Michael G. Gilman; Edward F. Kenehan, Jr.

[57] ABSTRACT

There is provided a process for producing aromatic hydrocarbons. The process involves contacting one or more non-aromatic compounds, such as propane, propylene, or methanol, with a catalyst containing a zeolite, such as ZSM-5. The zeolite is modified with phosphorus oxide by impregnating the zeolite with a source of phosphate ions, such as an aqueous solution of an ammonium phosphate, followed by calcination.

12 Claims, No Drawings

AROMATIZATION REACTIONS WITH ZEOLITES CONTAINING PHOSPHORUS OXIDE

BACKGROUND

The present invention relates to aromatization reactions with zeolites, such as, ZSM-5, containing an oxide of phosphorus.

The Chester et al U.S. Pat. No. 4,350,835 describes a process for converting ethane to liquid aromatics by contacting the ethane with a zeolite catalyst such as ZSM-5 having incorporated therein a minor amount of gallium.

The Davies et al U.S. Pat. No. 4,175,057 describes a process for producing aromatics by contacting a $C_3$–$C_8$ hydrocarbon with a gallium catalyst supported on an aluminosilicate in which the ratio of silica to alumina is between 20:1 and 70:1.

The Bulford et al U.S. Pat. No. 4,157,356 describes a process for producing aromatic hydrocarbons by contacting a $C_3$–$C_8$ hydrocarbon with a gallium catalyst on a silica support which has a surface area greater than 500 $m^2$/g and a pore volume less than 0.8 ml/g.

The Butter et al U.S. Pat. No 3,972,832 and the Kaeding et al U.S. Pat. No. 3,911,041 describe the treatment of various zeolites with phosphorus compounds which are capable of reacting or exchanging with hydrogen in zeolites followed by calcination. This particular phosphorus treatment is taught to result in the substantial reduction of aromatization activity of the zeolites. For example, note column 6, line 59 to column 7, line 13 of the Butter et al patent and column 7, lines 34–57 of the Kaeding et al patent.

The entire disclosures of the above-mentioned U.S. Patents are expressly incorporated herein by reference.

SUMMARY

According to one aspect of the present invention, there is provided a process for producing aromatic hydrocarbons, said process comprising contacting a feedstock comprising one or more non-aromatic compounds with a catalyst comprising a crystalline zeolite material having a constraint index within the approximate range of 1 to 12, said contacting taking place under sufficient aromatization conditions, said catalyst further comprising an oxide of phosphorus which has been incorporated into said catalyst by a process comprising the steps of:

(i) impregnating said zeolite with a source of phosphate ions; and (ii) calcining the impregnated zeolite of step (i) under conditions sufficient to convert said impregnated phosphate ions to said oxide of phosphorus.

EMBODIMENTS

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Although zeolites may contain silica and alumina, it is recognized that the silica and alumina portions may be replaced in whole or in part with other oxides. More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

An important characteristic of the crystal structure of the particular class of zeolites suitable for use in accordance with the present invention is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves of the aluminosilicate zeolites being bonded to the silicon or aluminum atoms at the centers of the tetrahedra. Briefly, the preferred type of aluminosilicate zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels Although aluminosilicate zeolites with a silica to alumina mole ratio of at least 12 are useful, it is preferred in some instances to use aluminosilicate zeolites having substantially higher silica/alumina ratios, e.g. 70 and above, 200 and above or even 1600 and above. In addition, aluminosilicate zeolites as otherwise characterized herein but which are substantially free of aluminum, that is zeolites having silica to alumina mole ratios of up to infinity, are found to be useful and even preferable in some instances. Such "high silica" or "highly siliceous" aluminosilicate zeolites are intended to be included within this description. Thus also to be included within the aluminosilicate zeolite definition are substantially pure silica forms of the useful zeolites described herein, that is to say those aluminosilicate zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

Constraint Index =
$$\frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraints Index (CI) values for some typical materials are:

| Zeolite | C.I. |
|---|---|
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 1.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The descriptions contained within those patents include the X-ray diffraction pattern of therein disclosed ZSM-5.

ZSM-11 is described in U.S. Pat. No. 3,709,979. The description in that patent includes the X-ray diffraction pattern of said ZSM-11.

ZSM-12 is described in U.S. Pat. No. 3,832,449. The description in that patent includes the X-ray diffraction pattern for ZSM-12.

ZSM-23 is described in U.S. Pat. No. 4,076,842 along with a specification of the X-ray diffraction pattern of the disclosed ZSM-23 zeolite.

ZSM-35 is described in U.S. Pat. No. 4,016,245 along with a description of the X-ray diffraction pattern of the zeolite.

ZSM-38 is more particularly described in U.S. Pat. No. 4,046,859. The description of that zeolite in that patent includes the X-ray diffraction pattern of ZSM-38.

ZSM-48 is more particularly described in U.S. Pat. No. 4,375,573. Such a description includes the X-ray diffraction pattern for ZSM-48.

It is to be understood that by incorporating by reference the foregoing patent documents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of aluminosilicate zeolites wherein the mole ratio of silica to alumina is essentially unbounded. The incorporation of the identified patent documents should therefore not be construed as limiting the disclosed crystalline zeolites to those having the specific compositions, e.g., silica-alumina mole ratios discussed therein, it now being known that such aluminosilicate zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

The dry density for known aluminosilicate zeolites may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite can be employed. Such other forms of the zeolite are those wherein the original alkali metal content has been reduced to less than about 50 percent by weight of the original alkali metal contained in the zeolite as synthesized, usually 0.5 percent by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing conversion processes using the catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

An additional component of the conversion catalysts in accordance with the present invention comprises a minor proportion, e.g., from about 0.05% to 50% by weight of the catalyst composite, of a phosphorus oxide, incorporated into the zeolite. Phosphorus, for example, can be incorporated into such catalysts at least in part in the form of phosphorus oxide in an amount of, e.g., from about 0.25% to about 25% by weight of the catalyst composition, preferably from about 0.7% to about 15% by weight. Such incorporation can be readily effected by contacting the zeolite composite with a solution of an appropriate phosphate compound, followed by drying and calcining to convert phosphorus in the zeolite to its oxide form. Particularly preferred are ammonium phosphates, including ammonium hydrogen phosphate, $(NH_4)_2HPO_4$, and ammonium dihydrogen phosphate, $NH_4H_2PO_4$. Calcination is generally conducted in the presence of oxygen at a temperature of at least about 150° C. However, higher temperatures, i.e., up to about 500° C. or higher are preferred. Such heating is generally carried out for 3-5 hours but may be extended to 24 hours or longer.

It will be understood that phosphate ions, being negatively charged, are incapable of exchanging or reacting with hydrogen in zeolites in the manner of the phosphorus compounds, such as trimethylphosphite, described in the aforementioned Butter et al U.S. Pat. Nos. 3,972,832 and the Kaeding et al 3,911,041. It is further noted that the zeolites, which are contacted with phosphate ions in accordance with the present invention, need not be in the hydrogen form. More particularly, when the zeolites are contacted with phosphate ions, the cation exchange sites of the zeolite may be occupied with cations other than hydrogen, which cations can later be calcined or exchanged to produce catalytically active hydrogen sites. Ammonium cations are preferred cations for occupying cation exchange sites of the zeolite when this zeolite is contacted with phosphate ions. Such ammonium cations are converted to hydrogen when the zeolite is calcined to convert phosphate ions to phosphorus oxide.

Additional catalyst modifying procedures which may also optionally be employed to modify catalyst activity or selectivity include precoking and presteaming (e.g., before oxide incorporation), or combinations thereof.

The aromatization conditions suitable for use in accordance with the present invention may include, e.g., a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The feedstock to be aromatized may comprise, e.g. $C_2$–$C_{12}$ non-aromatic hydrocarbons, $C_1$–$C_5$ alcohols, $C_2$–$C_6$ ethers and/or other non-aromatic compounds capable of producing aromatic compounds. Examples of $C_2$–$C_{12}$ non-aromatic hydrocarbons include ethylene, propylene and/or propane. When these three hydrocarbons are present in admixture, the feedstock to be aromatized may comprise, e.g., from about 1 to about 30 weight percent of ethylene, from about 1 to about 30 weight percent of propylene and from about 1 to about 30 weight percent of propane. This feedstock may be, e.g., a refinery off gas. An example of an alcohol which may be aromatized is methanol and an example of an ether which may be aromatized is dimethylether.

The phosphorus oxide modified zeolites in accordance with the present invention have been observed to have at least one of the following characteristics in aromatization reactions in comparison with corresponding non-phosphorus oxide modified zeolite: (1) they produce less aromatics having 9 or more, especially 10 or more carbon atoms (i.e. $C_9^+$ and $C_{10}^+$ aromatics); (2) they produce more benzene; and/or (3) they have more activity in terms of overall feedstock conversion. At the same time, these phosphorus oxide modified zeolites have been observed to produce BTX (i.e. a combination of benzene, toluene, xylene and/or ethylbenzene) in an amount of at least 95 percent by weight or even greater than 100 percent by weight of the amount produced by the corresponding non-phosphorus modified zeolites.

EXAMPLE 1

Modification of ZSM-5 containing 35% alumina binder was made by treating 200 g zeolite in a solution of 80 g diammonium hydrogen phosphate in 300 ml water at about 80° C. for 2 hours. The, thusly, phosphorus impregnated zeolite was then filtered, dried and calcined at 500° C. for 2 hours. The resulting P-ZSM-5 contained 3.54% by weight phosphorus.

Conversion of hydrocarbons was carried out by placing 5.0 g catalyst in a Quartz reactor and passing through 40 cc/min of the desired hydrocarbon at the desired temperature. The results are listed below in Tables 1-3 together with the results for comparison from the corresponding non-phosphorus oxide modified catalyst (i.e., HZSM-5).

TABLE 1

| | Conversion of Propane | | | | | |
|---|---|---|---|---|---|---|
| Catalyst | HZSM-5 | | | PZSM-5 | | |
| Temperature °C. | 500 | 550 | 600 | 500 | 550 | 600 |
| % Conversion | 41.5 | 85 | 96.4 | 70 | 95.4 | 99.8 |
| Wt % Selectivity | | | | | | |
| Benzene | 11.4 | 16.8 | 24.2 | 12.7 | 21.3 | 30.5 |
| BTX | 32.5 | 36.7 | 40.4 | 31.7 | 38.2 | 40.8 |
| $C_9^+$ aromatics | 5.7 | 6.2 | 5.6 | 3.8 | 3.4 | 4.3 |

TABLE 2

| | Conversion of Propylene | | | |
|---|---|---|---|---|
| Catalyst | HZSM-5 | | PZSM-5 | |
| Temperature °C. | 550 | 600 | 550 | 600 |
| % Conversion | 98 | 99 | 98 | 99 |
| Wt % Selectivity | | | | |
| Benzene | 22.5 | 31.1 | 21.7 | 32.5 |
| BTX | 59.3 | 56.5 | 57.1 | 62.3 |
| $C_9^+$ aromatics | 7.5 | 15.7 | 5 | 6 |

TABLE 3

| | Conversion of Simulated Refinery Off Gas | | | | | |
|---|---|---|---|---|---|---|
| Catalyst | HZSM-5 | | | PZSM-5 | | |
| Temperature °C. | 500 | 550 | 600 | 500 | 550 | 600 |
| Wt % in Products | | | | | | |
| Benzene | 5.2 | 9.1 | 12.0 | 6.0 | 10.4 | 14.1 |
| BTX | 16.6 | 18.5 | 17.1 | 17.6 | 20.6 | 21.8 |
| $C_9^+$ aromatics | 1.6 | 1.9 | 2.6 | .9 | 1.0 | 2.3 |

PZSM-5 gave higher benzene and BTX yields for all reactions and higher activity for propane conversions It is noted that the simulated refinery off gas of Table 3 included 22.6% ethane, 15.1% ethylene, 6.7% propane and 16% propylene

EXAMPLE 2

In this Example methanol was converted over PZSM-5 in comparison with HZSM-5. The PZSM-5 gave higher yields of BTX, higher yields of $C_5$–$C_9$ hydrocarbons and decreased yields of $C_{10}^+$ aromatics.

Two catalysts were used for comparison, an unmodified HZSM-5 and a PZSM ™ 5, prepared from the same crystals as A. The procedures for preparing the PZSM-5 were as follows: 50g ZSM-5 in ammonium form was treated with a solution of 10g diammonium hydrogen phosphate in 80ml water at about 80° C. for 4 hours. After drying at 60°–80° C. for 16 hours and calcination at 500° C., analyses showed that it contained 2.7% by weight P.

Methanol conversion was run at 400° and 450° C. over 5.0 g catalyst at WHSV = 1.3. Results are shown below in Table 4. Methanol conversion was complete in all cases.

TABLE 4

| | Conversion of Methanol | | | |
|---|---|---|---|---|
| Catalyst | HZSM-5 | | PZSM-5 | |
| Temperature °C. | 400 | 450 | 400 | 450 |
| Wt % Product | | | | |
| $C_1$–$C_3$ | 17.9 | 32.4 | 18.7 | 31.0 |
| $C_4$ | 27.4 | 22.6 | 26.9 | 23.2 |
| $C_5^+$ aliphatics | 21.5 | 8.1 | 19.4 | 9.7 |
| Benzene | .9 | 2.6 | 1.6 | 3.0 |
| Toluene | 6.4 | 10.4 | 11.5 | 13.7 |
| $C_8$ aromatics | 14.8 | 14.2 | 16.2 | 15.0 |
| $C_9$ aromatics | 7.8 | 6.4 | 4.3 | 2.9 |
| $C_{10}^+$ aromatics | 3.2 | 3.5 | 1.3 | 1.6 |
| BTX | 22.2 | 27.2 | 29.4 | 31.7 |
| $C_4$–$C_9$ | 51.5 | 41.6 | 53.0 | 44.2 |

The results show that for a given temperature, PZSM-5 gave higher BTX yields than HZSM-5. PZSM-5 also gave higher yields of $C_5$ to $C_9$ range hydrocarbons, a gasoline range, than HZSM-5. In this range, the higher yield of toluene would also result in higher octane gasoline.

The $C_9^+$ aromatics were noticeably lower than PZSM-5, especially those of $C_{10}^+$ aromatics, in which the yield of durene is also lower than HZSM-5.

The zeolites in this Example contain 35% alumina binder.

What is claimed is:

1. A process for producing aromatic hydrocarbons, said process comprising contacting a feedstock comprising one or more non-aromatic compounds selected from the group consisting of $C_2$–$C_{12}$ alkanes, $C_2$–$C_{12}$ alkenes, $C_1$–$C_5$ alcohols and $C_2$–$C_{12}$ ethers with a catalyst comprising a crystalline zeolite material having the structure of ZSM-5 or ZSM-11, said contacting taking under aromatization conditions including a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20, said catalyst further comprising an oxide of phosphorus which has been incorporated into said catalyst by a process comprising the steps of:
   (i) impregnating said zeolite with a source of phosphate ions; and
   (ii) calcining the impregnated zeolite of step (i) under conditions sufficient to convert said impregnated phosphate ions to said oxide of phosphorus.

2. A process according to claim 1, wherein said source of phosphate ions is an aqueous solution of an ammonium phosphate.

3. A process according to claim 2, wherein said ammonium phosphate is selected from the group consisting of $(NH_4)_2HPO_4$ and $NH_4H_2PO_4$.

4. A process according to claim 3, wherein essentially all of the cationic exchange sites of said zeolites are occupied by ammonium ions prior to and during the impregnation of said zeolite with said ammonium phosphate.

5. A process according to claim 1, wherein said zeolite material is an aluminosilicate zeolite having a silica/alumina mole ratio of at least 12.

6. A process according to claim 1, wherein said zeolite material has the structure of ZSM-5.

7. A process according to claim 1 wherein said catalyst further comprises a binder.

8. A process according to claim 1, wherein said feedstock comprises from about 1 to about 30 weight percent of ethylene, from about 1 to about 30 weight percent of propylene and from about 1 to about 30 weight percent of propane.

9. A process according to claim 1, wherein said feedstock comprises a refinery off gas.

10. A process according to claim 1, wherein said feedstock comprises ethylene, propane or propylene.

11. A process according to claim 1, wherein said feedstock comprises methanol.

12. A process according to claim 1, wherein said feedstock comprises dimethylether.

* * * * *

UNITED STATES PATENT AND TRADEMARK OFFICE
CERTIFICATE OF CORRECTION

PATENT NO. : 4,590,321

DATED : May 20, 1986

INVENTOR(S) : Chin-Chiun Chu

It is certified that error appears in the above-identified patent and that said Letters Patent is hereby corrected as shown below:

Column 10, line 14, change "than" to --with--.

Column 10, line 23, change "$C_2$-$C_{12}$" to --$C_2$-$C_6$--.

Column 10, line 26, --place-- should precede "under".

Signed and Sealed this

Fifteenth Day of September, 1987

*Attest:*

DONALD J. QUIGG

*Attesting Officer*    *Commissioner of Patents and Trademarks*